(12) United States Patent
Eto et al.

(10) Patent No.: US 11,016,083 B2
(45) Date of Patent: May 25, 2021

(54) METHOD FOR SCREENING FOR PLATELET PRODUCTION PROMOTERS

(71) Applicants: Kyoto University, Kyoto (JP); Megakaryon Corporation, Kyoto (JP)

(72) Inventors: Koji Eto, Kyoto (JP); Hideya Seo, Kyoto (JP); Akira Ota, Kyoto (JP); Yukitaka Ito, Kyoto (JP); Yasuko Hazama, Kyoto (JP)

(73) Assignees: Kyoto University, Kyoto (JP); Megakaryon Corporation, Kyoto (JP)

( * ) Notice: Subject to any disclaimer, the term of this patent is extended or adjusted under 35 U.S.C. 154(b) by 338 days.

(21) Appl. No.: 16/071,716

(22) PCT Filed: Jan. 30, 2017

(86) PCT No.: PCT/JP2017/003169
§ 371 (c)(1),
(2) Date: Jul. 20, 2018

(87) PCT Pub. No.: WO2017/131228
PCT Pub. Date: Aug. 3, 2017

(65) Prior Publication Data
US 2019/0033296 A1 Jan. 31, 2019

(30) Foreign Application Priority Data
Jan. 29, 2016 (JP) .............................. JP2016-016676

(51) Int. Cl.
*C12N 15/09* (2006.01)
*C12Q 1/6897* (2018.01)
*G01N 33/50* (2006.01)
*C12N 15/10* (2006.01)

(52) U.S. Cl.
CPC ......... *G01N 33/5023* (2013.01); *C12N 15/09* (2013.01); *C12N 15/1086* (2013.01); *C12Q 1/6897* (2013.01); *G01N 33/5044* (2013.01)

(58) Field of Classification Search
CPC ............................... C12N 15/09; C12Q 1/6897
See application file for complete search history.

(56) References Cited

U.S. PATENT DOCUMENTS

| 2008/0060087 A1 | 3/2008 | Kallies |
| 2012/0238023 A1 | 9/2012 | Eto et al. |
| 2014/0127815 A1 | 5/2014 | Eto et al. |
| 2014/0227780 A1 | 8/2014 | Nishino et al. |

FOREIGN PATENT DOCUMENTS

| JP | 2007521820 A | 8/2007 | |
| WO | 2008078453 A1 | 7/2008 | |
| WO | 2014168255 A1 | 10/2014 | |
| WO | WO-2014168255 A1 * | 10/2014 | ................ A61P 7/00 |
| WO | 2016143836 A1 | 9/2016 | |

OTHER PUBLICATIONS

Orth et al., Analysis of mitosis and antimitotic drug responses in tumors by in vivo microscopy and single-cell pharmacodynamics. Therapeutics, Targets, and Chemical Biology, vol. 71, No. 13 (Jul. 1, 2011) pp. 4608-4616 (Year: 2011).*
Seo et al., A β1-tubulin-based megakaryocyte maturation reporter system identifies novel drugs that promote platelet production. Blood Advances, vol. 2, No. 17 (Sep. 11, 2018) pp. 2262-2272 (Year: 2018).*
Chen et al., A novel megakaryocyte-based screening system identifies compounds that promote megakaryocyte maturation and platelet production in vitro. Blood (Dec. 7, 2017) 130 (Supplement 1): 2329. (Year: 2017).*
International Search Report received in PCT/JP2007/071220 dated Mar. 7, 2017.
Written Opinion received in PCT/JP2007/071220 dated Mar. 7, 2017.
Hirata, et al., "Congenital amegakaryocytic thrombocytopenia iPS cells exhibit defective MPL-mediated signaling", Aug. 1, 2013, pp. 3802-3814, vol. 123, No. 9, Publisher: J Clin Invest.
Ng, et al., Apr. 22, 2014, pp. 5884-5889, vol. 111, No. 16, Publisher: Proc. Natl. Acad. Sci.
Nieswandt, et al., "Megakaryocyte rupture for acute platelet needs", May 11, 2015, pp. 327-328, vol. 209, No. 3, Publisher: J Cell Biol.
Seo, et al., "Establishment of Megakaryocyte Maturation Promoting Drug Searching System to Which CRISPR/CAS9 Genome Editing Technique is Applied", Feb. 1, 2016, pp. 219, O-15-2, vol. 15, Suppl., Publisher: Journal of the Japanese Society for Regenerative Medicine, Regenerative Medicine Special Extra, (Partial Translation).
Takayama, et al., "Generation of functional platelets from human embryonic stem cells in vitro via ES-sacs, VEGF-promoted structures . . . hematopoietic progenitors", Jun. 1, 2008, pp. 5298-5306, vol. 111, No. 11, Publisher: Blood.
Ratz et al, "CRISPR/Cas9-mediated endogenous protein tagging for RESOLFT super-resolution microscopy of living human cells", Apr. 20, 2015, p. 9592 vol. 5, Publisher: Sci Rep.
Yang et al, "One-step generation of mice carrying reporter and conditional alleles by CRISPR/Cas-mediated genome engineering", 2013, pp. 1370-1379, vol. 154, No. 6, Publisher: Cell.

\* cited by examiner

*Primary Examiner* — Kara D Johnson
(74) *Attorney, Agent, or Firm* — Suzannah K. Sundby, Esq.; Canady + Lortz LLP (57) ABSTRACT

The present invention provides a method for screening for platelet production promoters, the method including a step for selecting a candidate substance that significantly increases expression of TUBB1 as a platelet production promoter.

5 Claims, 6 Drawing Sheets
Specification includes a Sequence Listing.

• MK FRACTION (VENUS FLUORESCENCE INTENSITY)

METHOD FOR SCREENING FOR PLATELET PRODUCTION PROMOTERS

REFERENCE TO A SEQUENCE LISTING SUBMITTED VIA EFS-WEB

The content of the ASCII text file of the sequence listing named "20180720_101621_007US1_seq", which was filed in PCT/JP2017/003169 on Jan. 30, 2017, downloaded from the WIPO database, is 1.66 kb in size with a created date of Feb. 8, 2017, and electronically submitted via EFS-Web herewith the application, is incorporated herein by reference in its entirety.

TECHNICAL FIELD

The present invention relates to a novel method for screening for platelet production promoters.

BACKGROUND ART

Blood cells are required for the treatment of blood-related diseases and for surgical operations. Among blood cells, platelets, which are cells required for blood coagulation (hemostasis), proplatelets, and megakaryocyte cells, which are cells that produce platelets, are cells where the need is particularly high. Leukemia treatments, bone marrow transplantation, and anticancer therapies create great demand for platelets in particular, and the requirement for a stable platelet supply is thus acute.

To date, methods in which various types of stem cells are differentiated to obtain megakaryocyte cells and these are cultured to release platelets, have been developed as in vitro platelet production methods. Due to the creation of iPS cells, greater attention has been directed in recent years to the usefulness of pluripotent cells as an important source of cell therapies in regenerative medicine. To date, for example, Takayama et al. have succeeded in inducing the differentiation of human ES cells into megakaryocyte cells and platelets (Non-Patent Document 1).

CITATION LIST

Non-Patent Documents

Non-Patent Document 1: Takayama, N., et al., Blood, 111, pp. 5298-5306, 2008
Non-Patent Document 2: Ng, et al., Proc. Natl. Acad. Sci., 2014, Vol. 111, No. 16, pp. 5884-5889
Non-Patent Document 3: Nishimura, et al., JCB, 2015, Vol. 209, pp. 327-328
Non-Patent Document 4: Hirata, et al., J. Clin. Invest., 123(9), pp. 3802-3814

SUMMARY

Technical Problem

Thrombopoietin (TPO) is conventionally known to be a platelet growth factor. Prior to the present invention, TPO receptors in the form of c-MPL-dependent drugs were widely studied as candidate substances of platelet growth promoters. However, platelet count may decrease following the appearance of neutralizing antibodies in the bodies of patients administered the c-MPL ligand, human megakaryocyte cell growth and development factor (PEG-r HuMGDF). More recently, although TPO acts to promote increases in megakaryocyte cells and megakaryocyte cell maturation, it has been reported to have no direct effect on platelet release (Non-Patent Documents 2 and 3).

Moreover, although the majority of research on megakaryocyte cells has been conducted on mice, megakaryocyte cells may demonstrate different behavior in humans and mice as in congenital amegakaryocytic thrombocytopenia (CAMT) (Non-Patent Document 4). Even if systems using human cells were able to be used, there were problems in terms of stability, safety and ethics depending on the type of cells used.

Solution to Problem

Known examples of megakaryocyte cell maturation factors include GATA1, FOG1, NFE2 and TUBB1. The inventors of the present invention found that, among these marker genes, TUBB1 is superior as an indicator when searching for platelet production promoters, and produced a reporter cell line derived from human iPS cells that emits fluorescence corresponding to the expression level of TUBB1, thereby leading to completion of the present invention.

Namely, the invention of the present application includes the inventions indicated below.

(1) A method for screening for platelet production promoters, the method including a step for selecting a candidate substance that significantly increases expression of TUBB1 as a platelet production promoter.

(2) The method described in (1), including a step for contacting the candidate substance with a megakaryocyte cell or a progenitor cell thereof prior to the selection step.

(3) The method described in (1) or (2), wherein the expression level of TUBB1 is determined as the expression level of a reporter gene inserted into the gene locus of TUBB1.

(4) Megakaryocyte cells or progenitor cells thereof in which a reporter gene is inserted into the gene locus of TUBB1.

(5) The cells described in (4), wherein the megakaryocyte cells are immortalized megakaryocyte cells.

(6) The cells described in (4) or (5), wherein the megakaryocyte cells are derived from pluripotent stem cells.

(7) The cells described in (6), wherein the pluripotent stem cells are iPS cells.

(8) The cells described in any one of (5) to (7), wherein the cells are derived from a human.

Advantageous Effects of Invention

According to the screening method and cell line of the present invention, drugs or genes (siRNA) having an effect on megakaryocyte cell maturation or platelet production that have conventionally been difficult to evaluate can be evaluated both comprehensively and easily. In addition, the present invention is far superior to the prior art in that it enables platelet production promoters to be efficiently screened while relying only on TUBB1 without having to examine the expression levels of other megakaryocyte cell maturation factors such as GATA1, FOG1 or NFE2.

DESCRIPTION OF EMBODIMENTS (Method for Screening for Platelet Production Promoters)

The method for screening for platelet production promoters of the present invention comprises the step for selecting a candidate substance that significantly increases expression of TUBB1 as a platelet production promoter. In the case of using in the present description, a "platelet production promoter" in the broad sense refers to a drug that promotes production of platelets and increases the amount of platelets produced per unit time as a result thereof. Candidate substances of such drugs can be selected from known compound libraries accessible by a person with ordinary skill in the art. In addition, the candidate substances are not limited to a compound, salt thereof or derivative thereof, but rather may be an antibody or antibody fragment thereof, an antisense oligonucleotide, ribozyme or molecule that causes RNA interference (to be referred to as "RNAi") provided it brings about an increase in the expression of TUBB1 in megakaryocyte cells or progenitor cells thereof.

Microtubules are composed of heterodimers of α-tubulin and β-tubulin. β-tubulin has seven isotypes in humans. TUBB1 is a gene that encodes β1-tubulin, which is a type I isotype that is a member of the family of β-tubulin proteins. Since TUBB1 is a gene that is specifically expressed in megakaryocyte cells and platelets in the same manner as GATA1, FOG1 and NFE2, it is known to be a megakaryocyte cell maturation factor. In the present invention, a candidate substance that significantly increases expression of TUBB1 is evaluated as a platelet production promoter. Although it is possible to combine the use of other megakaryocyte cell maturation factors as indicators, the use of TUBB1 alone as an indicator for screening for platelet production promoters makes it possible to screen for platelet production promoters efficiently.

In the case of using in the present description, "increased expression" or "promotion of platelet production" refers to a state in which production has been increased by 5% or more, 10% or more, 20% or more, 30% or more, 40% or more, 50% or more, 60% or more, 70% or more, 80% or more, 90% or more or 100% or more in comparison with a control that can be suitably evaluated by a person with ordinary skill in the art. Substances that prominently increase expression of TUBB1 in comparison with a positive control can be evaluated as having a high level of platelet increasing action. A known platelet production promoter such as an AhR antagonist, and preferably StemRegenin1 (SR1) (Selleckchem), can be used as a positive control.

Changes in expression of TUBB1 can be confirmed by contacting a candidate substance with megakaryocyte cells or progenitor cells thereof. The platelet production promoter can be contacted with megakaryocyte cells or progenitor cells thereof in a medium. The expression level of a reporter gene inserted at the gene locus of TUBB1 may be evaluated instead of determining the expression level of TUBB1. A gene that encodes a fluorescent protein such as VENUS can be used as a reporter gene.

Insertion of a reporter gene can be carried out by a person with ordinary skill in the art using a known technology such as a genome editing technology in the manner of the CRISPR/Cas9 system (Cong, L., et al., 2013, Science, 339, 819-823), TALEN (transcription activator-like effector nuclease) (Cermak, T., et al., 2011, Nucleic Acids Res., 39: e82), or ZFN (zinc finger nuclease) (Kim, Y. G., et al., 1996, Proc. Natl. Acad. Sci. USA, 93: 1156-1160).

The step for selecting a platelet production promoter can be carried out repeatedly. For example, secondary screening or additional screening may be carried out following primary screening corresponding to the number of libraries of compounds subjected to screening or the number of ultimately required candidate substances. In addition, cutoff values at that time can be set by a person with ordinary skill in the art.

(Reporter Cell Line)

The reporter cell line of the present invention consists of megakaryocyte cells or progenitor cells thereof in which a reporter gene has been inserted into the gene locus of TUBB1. The megakaryocyte cells are preferably human-derived immortalized megakaryocyte cells.

In this Description, "megakaryocyte cells" are characteristically the largest cells present in the bone marrow in an organism and characteristically release platelets. They are also characterized by being positive for the CD41a, CD42a, and CD42b cell surface markers, and may also additionally express a marker selected from the group consisting of CD9, CD61, CD62p, CD42c, CD42d, CD49f, CD51, CD110, CD123, CD131, and CD203c. A "megakaryocyte cell", when multinucleated (polyploidization), has 16X to 32X genomes relative to that in an ordinary cell, and in this Description the term "megakaryocyte cells" by itself includes, insofar as the characteristic features indicated above are present, both multinucleated megakaryocyte cells and pre-multinucleated megakaryocyte cells. "Pre-multinucleated megakaryocyte cells" is also synonymous with "immature megakaryocyte cells" and "growth-phase megakaryocyte cells".

Immortalized megakaryocyte cells can be obtained by various known methods. A nonlimiting example of a megakaryocyte cell production method is the method described in WO 2011/034073. Using this method, immortalized megakaryocyte cells that can propagate indefinitely can be obtained by the overexpression of an oncogene and a polycomb gene in a "cell less differentiated than a megakaryocyte cell". In addition, immortalized megakaryocyte cells can also be obtained according to the method described in WO 2012/157586 by inducing the overexpression of an apoptosis suppression gene in a "cell less differentiated than a megakaryocyte cell", i.e., a megakaryocyte progenitor cell (also referred to in this Description simply as a "progenitor cell"). By terminating the overexpression of gene, these immortalized megakaryocyte cells undergo the development of multinucleation and release platelets.

A combination of the methods described in the aforementioned documents may be used to obtain the megakaryocyte cells. In this case, overexpression of an oncogene, overexpression of a polycomb gene, and overexpression of an apoptosis suppression gene may be carried out simultaneously or sequentially. For example, multinucleated megakaryocyte cells may be obtained by bringing about the overexpression of an oncogene and polycomb gene; inhibiting this overexpression; then bringing about the overexpression of an apoptosis suppression gene; and inhibiting this overexpression. In addition, multinucleated megakaryocyte cells may also be obtained by bringing about overexpression of the oncogene, overexpression of the polycomb gene, and overexpression of the apoptosis suppression gene all at the same time and then terminating these overexpressions at the same time. Multinucleated megakaryocyte cells may also be obtained by first inducing overexpression of the oncogene and polycomb gene and then inducing overexpression of the apoptosis suppression gene and terminating these overexpressions at the same time.

In this Description, a "cell less differentiated than a megakaryocyte cell" and a "megakaryocyte progenitor cell" denote a cell that has the capacity to differentiate into a megakaryocyte and that resides in various stages of differentiation from a hematopoietic stem cell lineage to a megakaryocyte cell. Nonlimiting examples of cells less differentiated than megakaryocytes are hematopoietic stem cells, hematopoietic progenitor cells, CD34-positive cells, and megakaryocyte-erythroid progenitor cells (MEP). These cells may be obtained by isolation from the bone marrow, umbilical cord blood, or peripheral blood, or may be obtained by inducing differentiation from pluripotent stem cells, e.g., ES cells, iPS cells, and so forth, which are even less differentiated cells.

In this Description, "oncogene" refers to a gene that induces the malignant transformation of a cell within an organism, and examples are MYC family genes (for example, c-MYC, N-MYC, L-MYC), SRC family genes, RAS family genes, RAF family genes, and protein kinase family genes such as c-Kit, PDGFR, and Abl.

In this Description, a "polycomb gene" is known as a gene that functions to circumvent cell senescence by negatively regulating the CDKN2a (INK4a/ARF) gene (Ogura et al., Saisei Igaku [Regenerative Medicine], Vol. 6, No. 4, pp. 26-32; Jesus Gill et al., Nature Reviews Molecular Cell Biology, Vol. 7, pp. 667-677, 2006; Proc. Natl. Acad. Sci. USA, Vol. 100, pp. 211-216, 2003). Nonlimiting examples of polycomb genes are BMI1, Mel18, Ring1a/b, Phc1/2/3, Cbx2/4/6/7/8, Ezh2, Eed, Suz12, HADC, and Dnmt1/3a/3b.

In this Description, "apoptosis suppression gene" refers to a gene that has the function of suppressing the apoptosis of a cell, and can be exemplified by the BCL2 gene, BCL-xL gene, Survivin gene, and MCL1 gene.

Overexpression of genes and termination of the overexpression can be performed by the methods described in WO 2011/034073, WO 2012/157586, WO 2014/123242, and Nakamura S. et al., Cell Stem Cell, 14, 535-548, 2014, and by other known methods and by methods based on the preceding.

Common conditions may be used for the megakaryocyte cell culture conditions in all of the embodiments of the present invention. For example, the temperature may be approximately 35° C. to approximately 42° C., approximately 36° C. to approximately 40° C., or approximately 37° C. to approximately 39° C., while 5% $CO_2$ and/or 20% $O_2$ may be used. Static culture or shake culture may be used. There are also no particular limitations on the shaking rate in the case of shake culture, and, for example, 10 rpm to 200 rpm, 30 rpm to 150 rpm, and so forth can be used.

By culturing megakaryocyte cells as described in the preceding in the platelet production method according to the present invention, the megakaryocyte cells undergo maturation and platelets are produced from their cytoplasm. This maturation of the megakaryocyte cells refers to multinucleation of the megakaryocyte cells and the release of platelets.

The functionality of these platelets can be evaluated through measurements carried out in accordance with known methods. For example, the amount of activated platelets can be measured using the PAC-1 antibody, which is an antibody that binds specifically to the integrin αIIBβ3 (glycoprotein IIb/IIIa, CD41a/CD61 complex) activation marker that is present on the membrane of activated platelets. The amount of activated platelets may also be measured using antibody to detect CD62b (P-selectin), which is likewise an activation marker for platelets. The amount of platelets can be measured, for example, using flow cytometry and carrying out gating with antibody to the activation-independent platelet markers CD61 or CD41, followed by detection of binding by PAC-1 antibody or anti-CD62P antibody to the platelets. These processes may be carried out in the presence of adenosine diphosphate (ADP).

Platelet functionality may also be evaluated by examining whether binding with fibrinogen in the presence of ADP occurs. The activation of integrin as required in the initial stage of thrombus formation is produced by the binding of fibrinogen by platelets. In addition, platelet functionality may also be evaluated by a method in which the thrombus formation capacity is visualized and observed in vivo, as shown in FIG. 6 in WO 2011/034073.

There are no particular limitations on the culture medium for the cultivation of the megakaryocyte cells, and known media suitable for the production of platelets from megakaryocyte cells, or media based thereon, may be used as appropriate. For example, a medium used for the culture of animal cells can be prepared to function as a basal medium. The basal medium can be exemplified by IMDM medium, medium 199 medium, Eagle's minimum essential medium (EMEM) medium, α-MEM medium, Dulbecco's modified Eagle's medium (DMEM) medium, Ham's F12 medium, RPMI 1640 medium, Fischer's medium, Neurobasal Medium (Life Technologies Corporation), and mixed media from the preceding.

The culture medium may contain serum or plasma or may be serum-free. As necessary, the medium may also contain one or more substances such as, for example, albumin, insulin, transferrin, selenium, fatty acid, trace elements, 2-mercaptoethanol, thiol glycerol, monothioglycerol (MTG), lipids, amino acids (for example, L-glutamine), ascorbic acid, heparin, nonessential amino acids, vitamins, growth factors, low molecular weight compounds, antibiotics, antioxidants, pyruvic acid, buffers, inorganic salts, and cytokines. The cytokines are proteins that promote blood cell differentiation and can be exemplified by vascular endothelial growth factor (VEGF), thrombopoietin (TPO), various TPO-like agents, stem cell factor (SCF), insulin-transferrin-selenite (ITS) supplement, and ADAM inhibitor. A preferred medium for the present invention is IMDM medium containing serum, insulin, transferrin, serine, thiolglycerol, ascorbic acid, and TPO. It may also contain SCF and may also contain heparin. The co-use of TPO and SCF is preferred. There are no particular limitations on the concentration of each, but the TPO can be approximately 10 ng/mL to approximately 200 ng/mL or approximately 50 ng/mL to approximately 100 ng/mL; the SCF can be approximately 10 ng/mL to approximately 200 ng/mL or approximately 50 ng/mL; and the heparin can be approximately 10 U/mL to approximately 100 U/mL or approximately 25 U/mL. A phorbol ester (for example, phorbol 12-myristate 13-acetate, PMA) may also be added.

Human serum is preferred when serum is used. In addition, human plasma and so forth may be used instead of serum. Using the method according to the present invention, platelets equivalent to those obtained using serum can be obtained even with the use of these components.

When a drug-responsive gene expression induction system, e.g., the Tet-on (registered trademark) or Tet-off (registered trademark) system, is used for overexpression of genes or the termination thereof, in the overexpression process the corresponding drug, for example, tetracycline or doxycycline, may be incorporated in the culture medium, and overexpression may be inhibited by its removal from the culture medium.

The step for culturing the megakaryocyte cells may be carried out in the present invention without feeder cells. As demonstrated in the following examples, the method according to the present invention can provide functional platelets even by culture in the absence of feeder cells.

In this Description, "feeder cells" refer to cells that are co-cultured with the target cells in order to adjust to the environment required for the culture of the cells (target cells) that are to be propagated or differentiated. Insofar as they are cells that can be distinguished from the target cells, the feeder cells may contain cells originating from the same species or may contain cells of heterologous origin. The feeder cells may be cells that have been treated with antibiotics or gamma radiation to be nonpropagating, or may be cells not thusly treated.

The disclosures in all the patent documents and non-patent documents cited in this Description are incorporated in their entirety in this Description by reference.

Example 1 iPS Cells

An immortalized megakaryocyte line (MKCL SeV2) was produced in accordance with the method described by Nakamura et al., Cell Stem Cell, 2014 by the introduction of Bcl-xL, c-Myc, and Bmi1 into iPS cells (SeV2: cells produced, in accordance with the method of WO 2010/134526, by the introduction of c-MYC, OCT3/4, SOX2, and KLF4 into neonate human fibroblasts using a sendai virus vector). iPS cells (MK iPS #12) were produced from the immortalized megakaryocyte line (MKCL SeV2) according to the method described by Okita K et al., Stem Cells, 31(3):458-466, 2013. The obtained iPS cells (MK iPS #12) were cultured in accordance with the method described by Nakagawa M et al., Sci Rep. 8; 4:3594, 2014 using StemFit (registered trademark) AK03 (Ajinomoto) and laminin 511 (iMatrix 511 (Nippi)).

Homologous Recombination

Figure 1A:
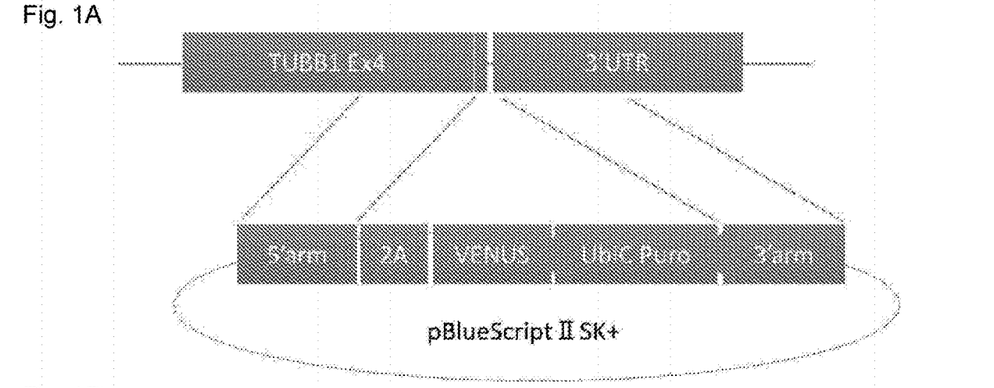
FIG. 1A is a structural diagram of pBlueScriptII SK+ (TUBB1-VENUS), which is a template vector.
Figure 1B:
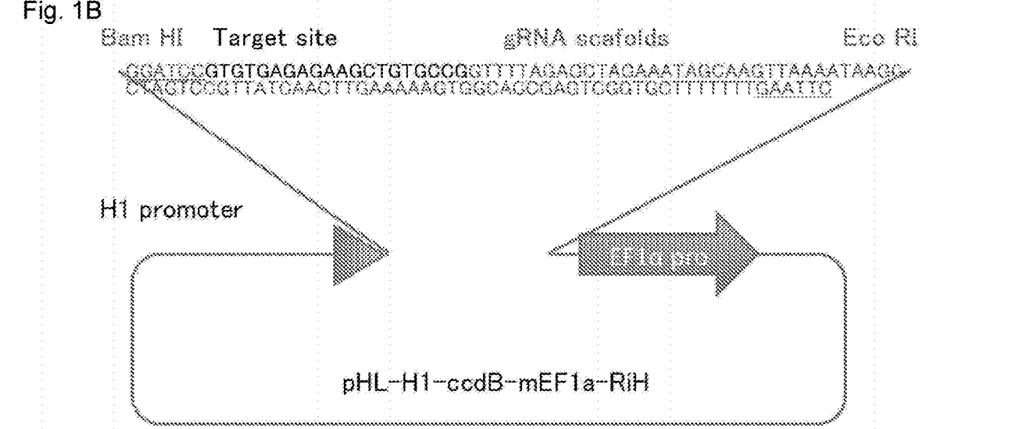
FIG. 1B is a structural diagram of pHL-H1-ccdB-mEF1a-RiH, which is a guide vector. The target sequence and neighboring sequences inserted in the guide vector are given as SEQ ID NO:1.

The cultured iPS cells (MK iPS #12) were dissociated using TrypLE (registered trademark) Select, and $0.8 \times 10^6$ cells were mixed with 1.7 μg template vector (FIG. 1A), 1.7 μg guide vector (FIG. 1B), and 1.7 μg cas9 vector (pHL-EF1a-SphcCas9-iC-A, received from Dr. Hotta, Center for iPS Cell Research and Application, Kyoto University), and the vectors were introduced into the cells by electroporation using a Human Stem Cell Nucleofector (registered trademark) Kit 2 (Lonza) and Nucleofector. After electroporation, suspension was carried out in StemFit (registered trademark) AK03 followed by seeding to a laminin 511-coated 10-cm dish and culture under conditions of 37° C. and 5% $CO_2$. After 3 days, puromycin was added to the culture medium at 1 ng/mL and subculturing was performed. After 7 days, the colonies that had formed were picked up and DNA was extracted from each of the obtained colonies using a QIAamp DNA Mini Kit (QIAGEN), and homologous recombination was confirmed by genotyping PCR using primers (TUBB1 insert check Fw and Rv, 5-1 insert check Fw and 5-1.2 insert check Rv, and 3-1.2 insert check Fw and 3-2 insert check Rv; the sequences are given in Table 1). The homozygous homologous recombinant iPS cell line was expansion cultured and established as MK iPS #12-23.

TABLE 1

| Primer | Sequence |
| --- | --- |
| TUBB1 insert check Fw | GATGCTTTACTGGTGCCCTT (SEQ ID NO: 2) |
| TUBB1 insert check Rv | AAGAGATGGCAGTGCTGCAT (SEQ ID NO: 3) |
| 5-1 insert check Fw | TGCTTTACTGGTGCCCTTCT (SEQ ID NO: 4) |
| 5-1.2 insert check Rv | AAGTCGTGCTGCTTCATGTG (SEQ ID NO: 5) |
| 3-1.2 insert check Fw | GCAACCTCCCCTTCTACGAG (SEQ ID NO: 6) |
| 3-2 insert check Rv | TCGGAGCATTTTCCCATTAC (SEQ ID NO: 7) |

The obtained MK iPS #12-23 was then mixed with 5 μg cre expression vector (pCXW-Cre-Puro, received from Dr. Hotta, Center for iPS Cell Research and Application, Kyoto University), and the vector was introduced into the cells by electroporation using a Human Stem Cell Nucleofector (registered trademark) Kit 2 (Lonza) and Nucleofector. After electroporation, suspension was carried out in StemFit (registered trademark) AK03 followed by seeding to a laminin 511-coated 10-cm dish and culture under conditions of 37° C. and 5% $CO_2$. After 9 days, multiple colonies were picked up and were divided in two: one half was cultured under the addition of puromycin at 1 ng/mL to the culture medium and the other half was stored. For stored cells deriving from the same colony for which cell death had been confirmed for the line, the removal of the puromycin resistance cassette was checked by genotyping PCR using primers (TUBB1 insert check Fw and Rv), and the resulting iPS cell line was expansion cultured to establish MK iPS #12-23 cre2.

Induction of Immortalized Megakaryocyte Cell Line

The induction of hematopoietic progenitor cells (HPC) was performed from the iPS cells (MK iPS #12-23 cre2) via iPS-sac. In more detail, the iPS cells were released from the culture dish using a cell scraper, and about one-twentieth of the cells were seeded as colony clusters onto mitomycin C (MMC)-treated C3H10T1/2 (available from Riken). The MMC-treated C3H10T1/2 was prepared by seeding $8 \times 10^5$ cells/dish to a 10-cm dish on the day prior to seeding with the iPS cells. After seeding, the culture was started (day 0) in Eagle's basal medium (EBM) supplemented with 20 ng/mL VEGF, in an environment of 5% $O_2$, 5% $CO_2$, and 37° C. Medium exchange with the same culture medium was performed at a frequency of twice per week.

The cells were physically released on day 14 using a cell scraper and the tip of a pipet, and cells of uniform size were recovered by passage through a 40-micrometer cell strainer.

On day 14, the cells were recovered and seeded into a 6-well dish at $1 \times 10^5$ cells/well on the MMC-treated C3H10T1/2 cells. EBM containing 50 ng/ml of SCF, 50 ng/ml of TPO and 0.5 μg/ml of doxycycline was used for the medium. On day 17, the cells were recovered by pipetting and seeded into a 10 cm dish at $1 \times 10^6$ cells/dish on MMC-treated C3H10T1/2 cells. The cells were recovered on day 23 and seeded into a 10 cm dish at $1 \times 10^6$ cells/dish to prepare the reporter immortalized megakaryocyte cell line (MKCL #12-23 cre2).

Production of Platelets

Figure 2A:
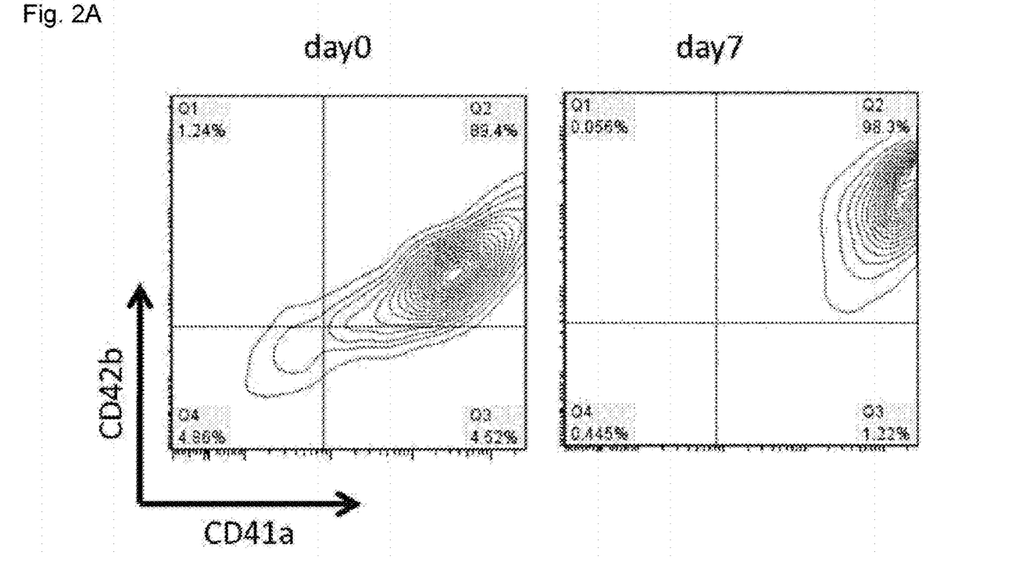
FIG. 2A gives the results of flow cytometric measurement of the distribution of cells expressing CD42b and CD41a for a reporter immortalized megakaryocyte line (MKCL #12-23 cre2).
Figure 2B:
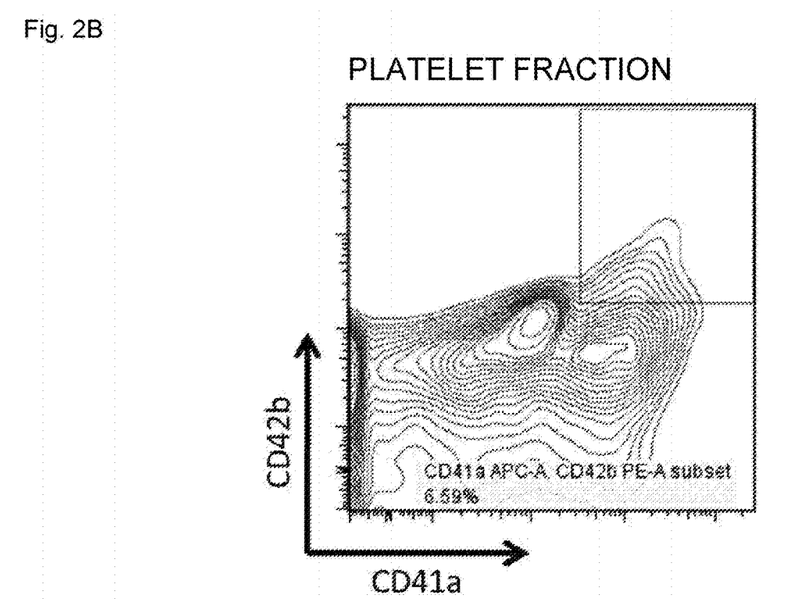
FIG. 2B gives the results of flow cytometric measurement of the distribution of cells expressing CD42b and CD41a for a fraction in which platelet production had been induced by culture on a differentiation medium that did not contain doxycycline.

Continuing, the megakaryocyte cells were cultured in differentiation medium not containing doxycycline to induce the release of platelets. More specifically, the reporter immortalized megakaryocyte cell line (MKCL #12-23 cre2) obtained according to the method described above was cultured for 7 days in differentiation medium containing 0.75 μM StemRegenin 1 (SR1) (Selleckchem), 10 μM Y-27632 (Wako), 50 ng/ml of TPO (R&D) and 50 ng/ml of SCF (R&D). After suspending the cultured cells, the cells were recovered from the culture supernatant and analyzed by FACS after staining with anti-CD41a antibody and anti-CD42b antibody. As a result, expression intensity of CD41a and CD42b was enhanced (megakaryocyte cell maturation was induced) by culturing for 7 days (FIG. 2A) and platelets positive for CD41a and CD42b were confirmed to have been produced from the megakaryocyte cell line as a result of culturing for 7 days (FIG. 2B).

Evaluation of Immortalized Megakaryocyte Cell Line

After culturing the immortalized megakaryocyte line obtained according to the method described above for 4 days on 10T1/2R feeder cells in differentiation medium containing 50 ng/ml of TPO and 50 ng/ml of SCF, the cells were stained with anti-CD41a antibody and anti-CD42b antibody and sorted into a VENUS high group and VENUS low group based on the expression level of VENUS as determined by FACS.

A cell group cultured for 4 days in differentiation medium containing 50 ng/ml of TPO and 50 ng/ml of SCF or differentiation medium containing 0.75 μM SR1, 10 μM Y-27632, 50 ng/ml of TPO and 50 ng/ml of SCF was used as a control (designated as an SR1+rocki group and plain group, respectively).

Figure 3A:
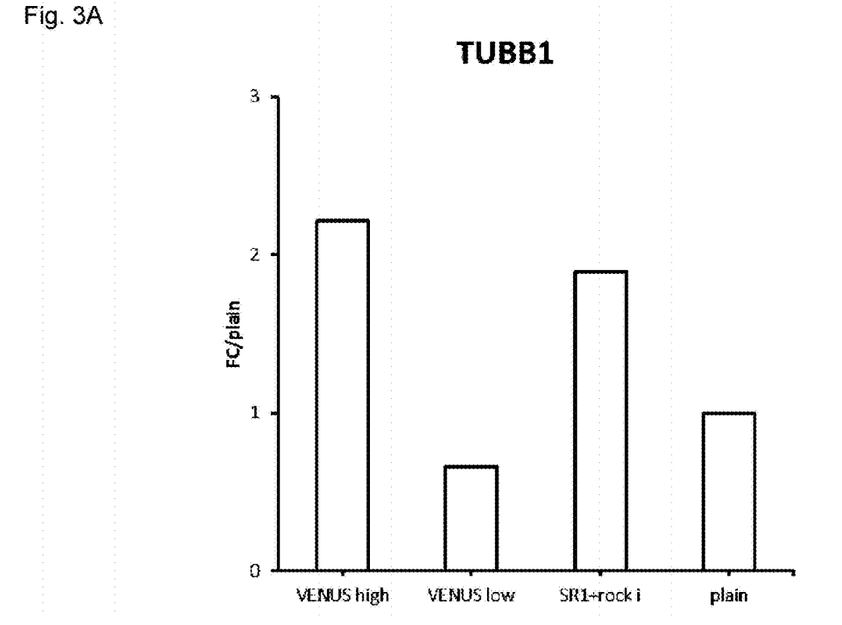
FIG. 3A indicates the results of measuring expression levels of TUBB1 by qPCR for a VENUS high group, a VENUS low group, an SR1+rocki (Y-27632) group and a plain group; and the ratio of the mRNA expression level is plotted on the vertical axis based on a value of 1 for the plain group.
Figure 3B:
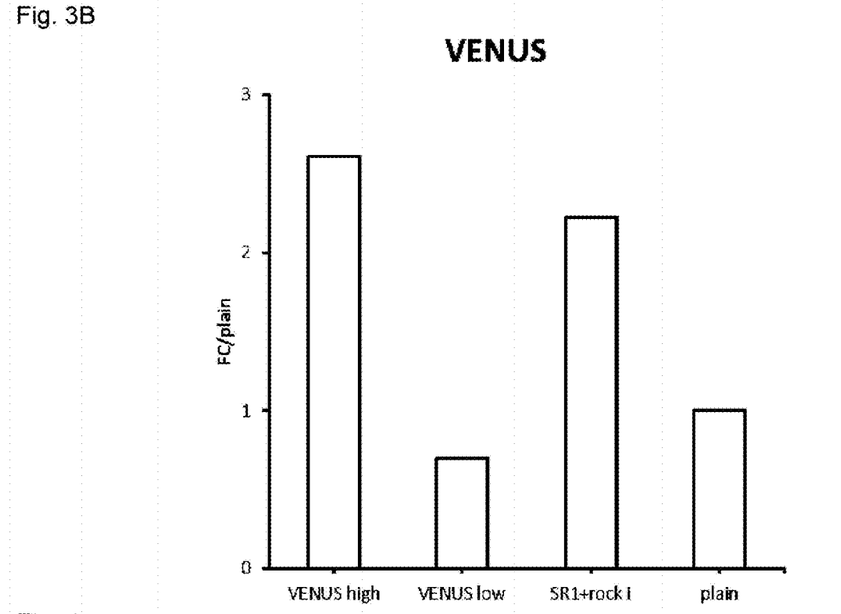
FIG. 3B indicates the results of measuring expression levels of VENUS by qPCR for a VENUS high group, a VENUS low group, an SR1+rocki (Y-27632) group and a plain group; and the ratio of the mRNA expression level of VENUS is plotted on the vertical axis based on a value of 1 for the plain group.
Figure 4:
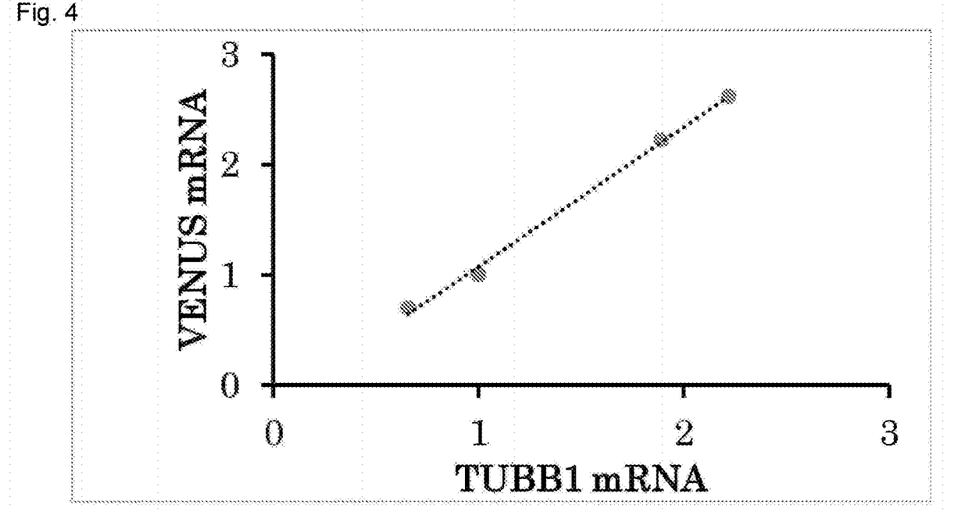
FIG. 4 is a graph indicating the correlation between the expression levels of TUBB1 and the expression levels of VENUS described in FIG. 3.

When the expression levels of TUBB1 and VENUS were measured by qPCR for the VENUS high group (high level of VENUS fluorescence intensity), VENUS low group (low level of VENUS fluorescence intensity), SR1+rocki group (Y-27632) and plain group, the expression levels of TUBB1 and VENUS were confirmed to be proportional (FIGS. 3 and 4).

Figure 5:
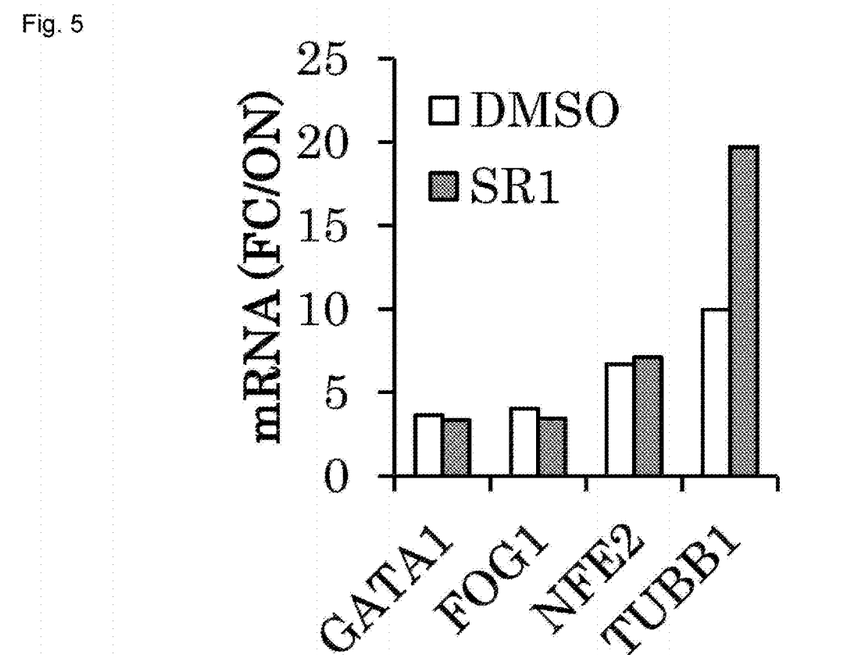
FIG. 5 represents the amount of change in the expression levels of each of the genes of TUBB1, GATA1, FOG1 and NFE2 in MKCL 12-23 cre2 in the presence of SR1 or DMSO (negative control).

On the basis of the above, the expression level of TUBB1 was confirmed to be able to be used interchangeably with the expression level of VENUS in the immortalized megakaryocyte cell line derived from MK iPS #12-23 cre2. Moreover, when the expression level of TUBB1 was compared with that of other megakaryocyte cell maturation factors, TUBB1 was clearly determined to be particularly superior as an indicator when searching for platelet production promoters. More specifically, as a result of measuring and comparing the expression levels of GATA1, FOG1, NFE2 and VENUS after culturing for 4 days in differentiation medium containing SR1 or DMSO from which doxycycline had been removed, the expression level of TUBB1 demonstrated the most favorable sensitivity (FIG. 5).

Figure 6A:
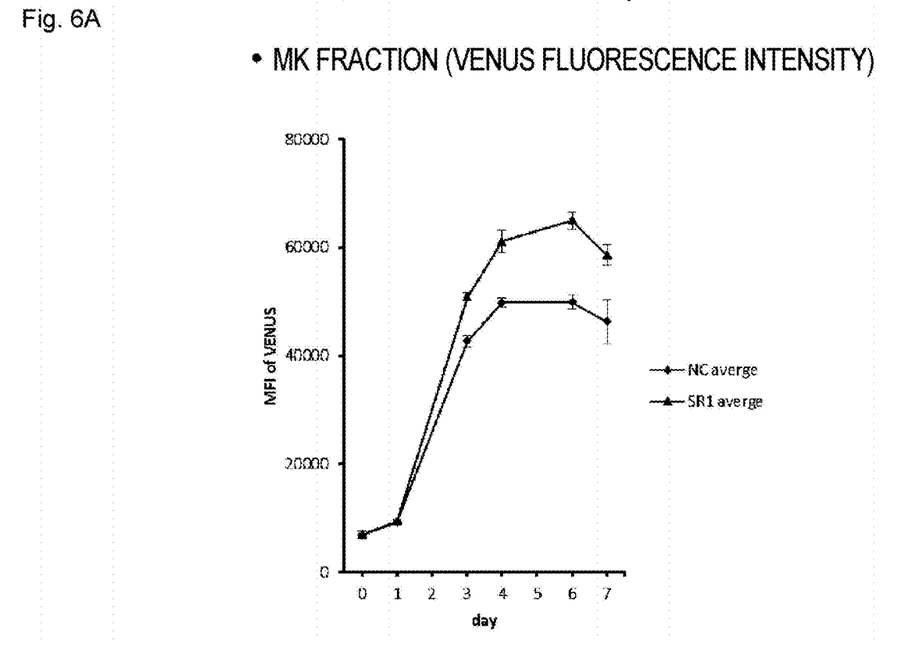
FIG. 6A is a graph indicating the results of analyzing the supernatant of immortalized megakaryocyte cell lines cultured in medium obtained by adding SR1 or DMSO (negative control) to a prescribed differentiation medium by FACS by staining with anti-CD41a antibody and anti-CD42b antibody; and VENUS fluorescence intensity is plotted on the vertical axis, the number of culturing days is plotted on the horizontal axis, and NC indicates the negative control.
Figure 6B:
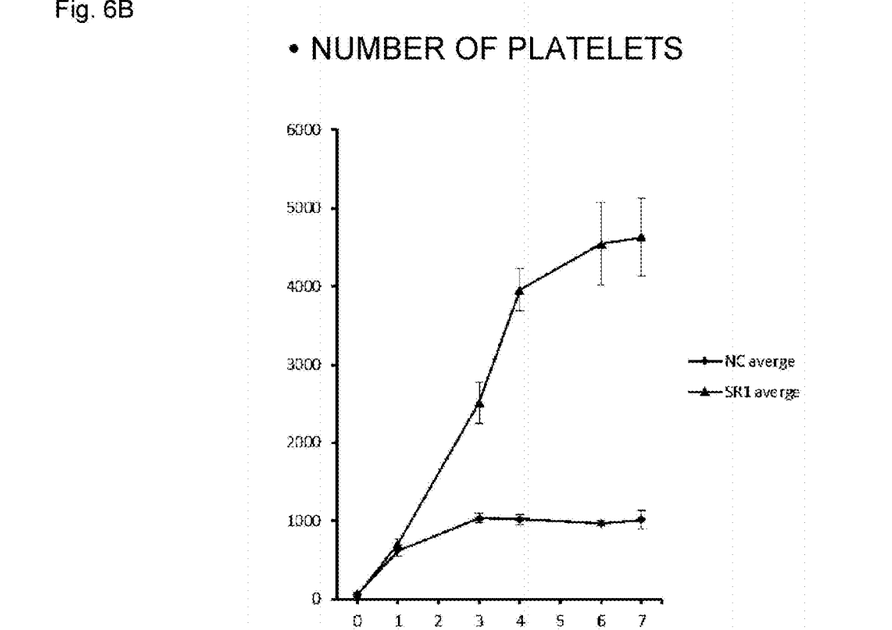
FIG. 6B indicates actual values obtained by measuring the numbers of platelets contained per unit volume based on the results of FIG. 6A; and the number of platelets contained per unit volume is plotted on the vertical axis, the number of culturing days is plotted on the horizontal axis, and NC indicates the negative control.
Figure 7:
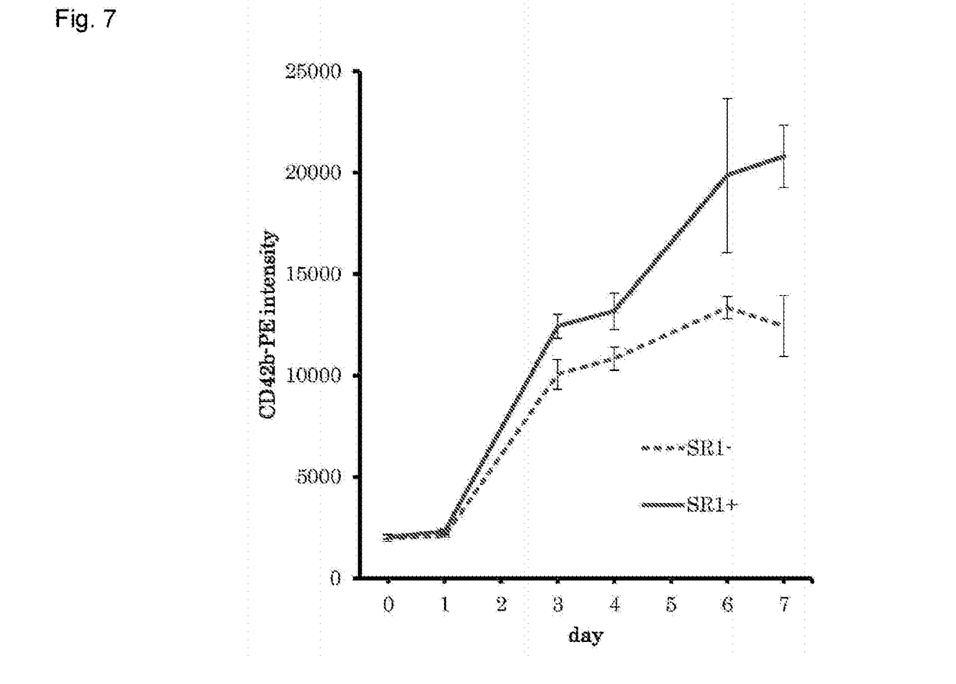
FIG. 7 indicates the results of FACS analysis under the conditions of FIG. 6A by staining with anti-CD42b antibody; CD42b-PE fluorescence intensity is plotted on the vertical axis, the number of culturing days is plotted on the horizontal axis, and NC indicates the negative control; and SR1$^+$ represents a cell group treated with SR1, while SR1$^-$ represents a DMSO-treated group.

Continuing, the immortalized megakaryocyte cell line was cultured on 10T1/2R feeder cells in differentiation medium containing 50 ng/ml of TPO and 50 ng/ml of SCF or differentiation medium containing 0.75 μM SR1, 10 μM Y-27632, 50 ng/ml of TPO and 50 ng/ml of SCF, followed by suspending the cells and harvesting the supernatant on day 0, day 1, day 3, day 4, day 6 and day 7 of culturing and analyzing the cells by FACS after staining with anti-CD41a antibody and anti-CD42b antibody. As a result, the expression level of VENUS was confirmed to rise and the number of platelets produced was confirmed to increase due to the addition of SR1 (FIGS. 6 and 7).

Screening for SR1 Substitutes

Figure 8:
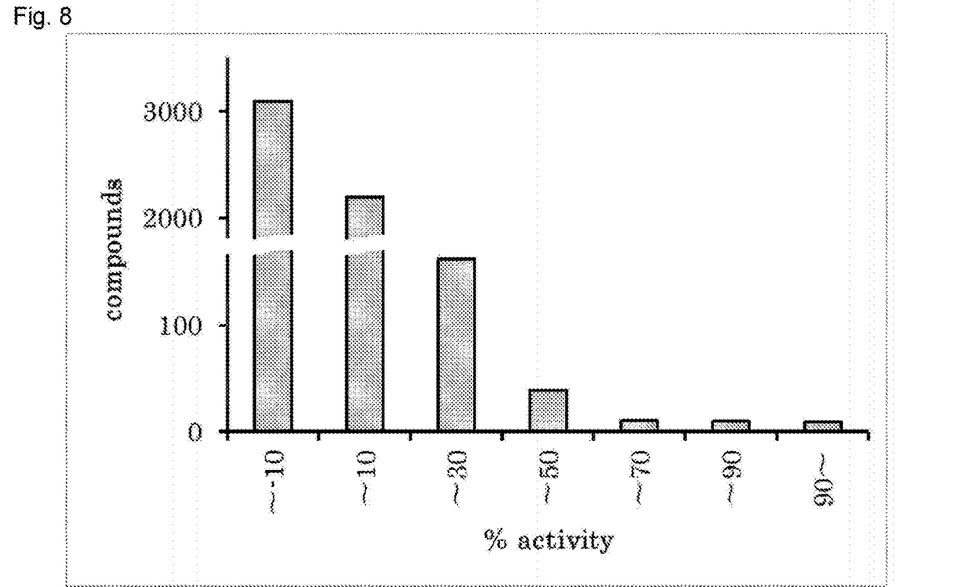
FIG. 8 indicates the results of measuring the fluorescence intensity of VENUS in immortalized megakaryocyte cells cultured in differentiation medium containing each of 5425 types of compounds using Array Scan VTI (Thermo Scientific) and categorizing according to activity (%); and the value of each activity level is represented with a histogram of values obtained by correcting the fluorescence intensity of each compound according to the fluorescence intensity of a positive control group (0.75 μM SR1 group assigned a value of 100%) and the fluorescence intensity of a negative control group (0.1% DMSO group assigned a value of 0%).

Primary screening consisted of seeding the immortalized megakaryocyte cell line obtained according to the method described above into a 96-well dish followed by culturing by adding 10 μM Y-27632, 50 ng/ml of TPO, 50 ng/ml of SCF and 1 μM of each compound obtained from a compound library provided by Professor Ohta of the Center for iPS Cell Research and Application (CiRA), Kyoto University (total of 5425 compounds, including duplicate compounds). The cells were also cultured in differentiation medium containing 0.75 μM SR1, 10 μM Y-27632, 50 ng/ml of TPO and 50 ng/ml of SCF (positive control) or differentiation medium containing 0.1% DMSO, 10 μM Y-27632, 50 ng/ml of TPO and 50 ng/ml of SCF (negative control). On day 7 of culturing, the fluorescence intensity of VENUS in each compound group was measured with Array Scan VTI (Thermo Scientific), and the value of fluorescence intensity of each compound was corrected according to the fluorescence intensity of the positive control (assigned a value of 100%) and the fluorescence intensity of the negative control (assigned a value of 0%) (FIG. 8). Those drugs for which this value was 30% or higher were selected as primary candidate compounds. The primary candidate compounds consisted of 67 types of compounds, and included, for example, TCS-359 (CAS NO. 301305-73-7, Santa Cruz Biotechnology, Inc.) and C59 (CAS NO. 1243243-89-1).

Secondary screening consisted of seeding the immortalized megakaryocyte cell line obtained according to the method described above into a 96-well dish and culturing after adding 10 μM Y-27632, 50 ng/ml of TPO, 50 ng/ml of SCF and the primary candidate compounds at concentrations of 10 μM, 3.3 μM, 1.1 μM and 0.4 μM each. The cells were also cultured in differentiation medium containing 0.75 μM SR1, 10 μM Y-27632, 50 ng/ml of TPO and 50 ng/ml of SCF (positive control) or differentiation medium containing 0.1% A DMSO, 10 μM Y-27632, 50 ng/ml of TPO and 50 ng/ml of SCF (negative control). On day 7 of culturing, the fluorescence intensity of VENUS in each compound group was measured with Array Scan VTI (Thermo Scientific), and the value of fluorescence intensity of each compound was corrected according to the fluorescence intensity of the positive control (assigned a value of 100%) and the fluorescence intensity of the negative control (assigned a value of 0%). Those drugs for which this value was 30% or higher and for which concentration dependency was observed were selected as secondary candidate compounds. The secondary candidate compounds consisted of 35 types of compounds, and included, for example, TCS-359 (CAS NO. 301305-73-7, Santa Cruz Biotechnology, Inc.) and C59 (CAS NO. 1243243-89-1).

Figure 9:
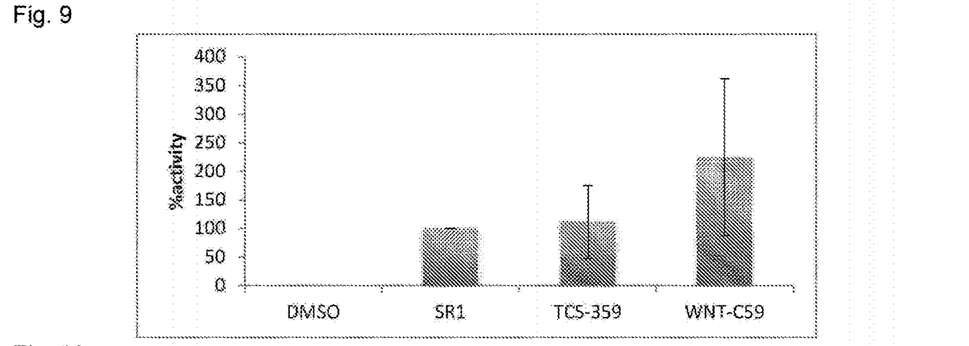
FIG. 9 is a graph representing the fluorescence intensity (number of platelets) of compounds consisting of 28 types of drugs judged to be positive in secondary screening that demonstrated an ability to produce platelets comparable to that of SR1 after correcting according to the platelet count in a positive control group (0.75 μM SR1 group assigned a value of 100%) and the platelet count in a negative control group (0.1% A DMSO group assigned a value of 0%).

Continuing, the effect of promoting platelet production was confirmed for 28 compounds from among the secondary candidate compounds excluding duplicate compounds and compounds that were unable to be used commercially. The above-mentioned immortalized megakaryocyte cell line was cultured in a 6-well dish in differentiation medium containing each of the compounds at concentrations of 10 μM, 3.3 μM, 1.1 μM and 0.4 μM, 10 μM Y-27632, 50 ng/ml of TPO and 50 ng/ml of SCF, differentiation medium containing 0.75 μM SR1, 10 μM Y-27632, 50 ng/ml of TPO and 50 ng/ml of SCF (positive control), or differentiation medium containing 0.1% DMSO, 10 μM Y-27632, 50 ng/ml of TPO and 50 ng/ml of SCF (negative control), followed by suspending the cells and harvesting the supernatant on day 7 of culturing and analyzing by FACS after staining with anti-CD41a antibody and anti-CD42b antibody. The relative number of platelets was calculated by correcting the number of platelets in the case of using each candidate compound with the number of platelets of the positive control (assigned a value of 100%) and the number of platelets of the negative control (assigned a value of 0%) (FIG. 9).

On the basis of the above results, compounds were discovered that have the potential to induce platelet production more potently than SR1 in excess of 100%. C59 in particular was suggested to be a potent platelet inducer.

Effects of C59 and TCS-359 on Platelet Production in Absence of Feeder Cells

Figure 10:
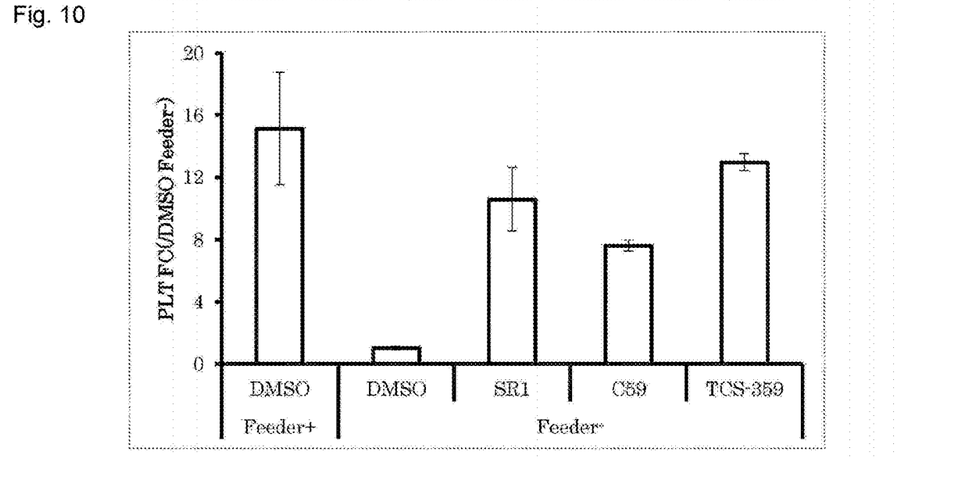
FIG. 10 indicates the results of comparing the platelet production volume of megakaryocyte cells (non-immortalized megakaryocyte cells) derived from iPS cultured in the absence of feeder cells in medium containing prescribed concentrations of SR1, C59 or TCS-359.

After culturing iPS cells (TkDA3-4), the colonies were detached with a cell scraper and cultured in differentiation medium on 10T1/2 feeder cells following the addition of 20 μg/ml of VEGF in accordance with Takayama, N., et al., Blood, 111, pp. 5298-5306, 2008. Fourteen days later, the cells were recovered using a cell scraper and cultured for 10 days in the absence of feeder cells following the addition of 25 U/mL of heparin, 10 μM Y-27632, 100 ng/ml of TPO and 50 ng/ml of SCF, and further adding 0.1% DMSO, 0.75 μM SR1, 1 μM C59 (Albiochem) or 3.3 μM TCS-359 (Santa Cruz Biotechnology, Inc.). Culturing was also carried out in the same manner using feeder cells. The resulting cells were suspended and the supernatant was harvested followed by analyzing by FACS after staining with anti-CD41a antibody and anti-CD42b antibody (FIG. 10). As a result, C59 and TCS-359 were confirmed to have the ability to produce platelets that was equal to or greater than that of SR1 in the absence of feeder cells.

On the basis thereof, C59 and TCS-359 were determined to increase platelet production capacity not only in MKCL, but also in megakaryocyte cells induced to differentiate from iPS cells. According to this result, C59 and TCS-359 were suggested to increase the platelet production capacity of megakaryocyte cells.

What is claimed is:

1. Megakaryocyte cells or progenitor cells thereof in which a reporter gene is inserted into the gene locus of TUBB1.

2. The cells according to claim 1, wherein the megakaryocyte cells are immortalized megakaryocyte cells.

3. The cells according to claim 1, wherein the megakaryocyte cells are derived from pluripotent stem cells.

4. The cells according to claim 3, wherein the pluripotent stem cells are iPS cells.

5. The cells according to claim 2, wherein the cells are derived from a human.

* * * * *

SEQUENCE LISTING

<160> NUMBER OF SEQ ID NOS: 7

<210> SEQ ID NO 1
<211> LENGTH: 115
<212> TYPE: DNA
<213> ORGANISM: Artificial Sequence
<220> FEATURE:
<223> OTHER INFORMATION: Target vector

<400> SEQUENCE: 1
ggatccgtgt gagagaagct gtgccggttt tagagctaga aatagcaagt taaaataagg     60
ctagtccgtt atcaacttga aaaagtggca ccgagtcggt gcttttttg aattc         115

-continued

```
<210> SEQ ID NO 2
<211> LENGTH: 20
<212> TYPE: DNA
<213> ORGANISM: Artificial Sequence
<220> FEATURE:
<223> OTHER INFORMATION: TUBB1 insert check Fw

<400> SEQUENCE: 2
gatgctttac tggtgccctt                                               20

<210> SEQ ID NO 3
<211> LENGTH: 20
<212> TYPE: DNA
<213> ORGANISM: Artificial Sequence
<220> FEATURE:
<223> OTHER INFORMATION: TUBB1 insert check Rv

<400> SEQUENCE: 3
aagagatggc agtgctgcat                                               20

<210> SEQ ID NO 4
<211> LENGTH: 20
<212> TYPE: DNA
<213> ORGANISM: Artificial Sequence
<220> FEATURE:
<223> OTHER INFORMATION: 5-1 insert check Fw

<400> SEQUENCE: 4
tgctttactg gtgcccttct                                               20

<210> SEQ ID NO 5
<211> LENGTH: 20
<212> TYPE: DNA
<213> ORGANISM: Artificial Sequence
<220> FEATURE:
<223> OTHER INFORMATION: 5-1.2 insert check Rv

<400> SEQUENCE: 5
aagtcgtgct gcttcatgtg                                               20

<210> SEQ ID NO 6
<211> LENGTH: 20
<212> TYPE: DNA
<213> ORGANISM: Artificial Sequence
<220> FEATURE:
<223> OTHER INFORMATION: 3-1.2 insert check Fw

<400> SEQUENCE: 6
gcaacctccc cttctacgag                                               20

<210> SEQ ID NO 7
<211> LENGTH: 20
<212> TYPE: DNA
<213> ORGANISM: Artificial Sequence
<220> FEATURE:
<223> OTHER INFORMATION: 3-2 insert check Rv

<400> SEQUENCE: 7
tcggagcatt ttcccattac                                               20
```